United States Patent [19]

Shutts

[11] Patent Number: 4,812,740
[45] Date of Patent: Mar. 14, 1989

[54] COATING DETECTOR FOR LOW EMISSIVITY GLASS

[76] Inventor: Christopher J. Shutts, 10128 Woodbury Dr., Wexford, Pa. 15090

[21] Appl. No.: 934,507

[22] Filed: Nov. 24, 1986

[51] Int. Cl.⁴ .............................................. G01R 27/00
[52] U.S. Cl. .................................... 324/62; 324/65 P; 324/158 P; 324/65 R
[58] Field of Search ................. 324/61 R, 61 P, 62 R, 324/65 R, 65 P, 72.5, 158 P

[56] References Cited

U.S. PATENT DOCUMENTS 4,504,781 3/1985 Hargrove ........................... 324/72.5

FOREIGN PATENT DOCUMENTS 664037 5/1950 United Kingdom .

Primary Examiner—A. D. Pellinen
Assistant Examiner—Leon K. Fuller
Attorney, Agent, or Firm—Hovey, Williams, Timmons & Collins

[57] ABSTRACT

A detector for sensing the electrical conductivity of planar surfaces, such as glass panels having an electrical conductive, low emissivity coating on one side thereof, includes a housing carrying a battery and an LED, and a pair of spaced apart contact elements electrically coupled to the battery and LED. Structure is provided for rigidly connecting the pair of contact elements to a outer wall of the housing and for supporting an outer portion of the contact elements a fixed distance away from the housing for enabling the outer portions of both of the contact elements to directly and simultaneously engage the planar glass coating as soon as the housing is shifted to a position adjacent the glass. The housing is of a configuration adapted to be carried by the human hand, and the LED is mounted on a wall of the housing opposite a housing wall supporting the contact elements, so that the detector can be held by one hand of the worker and moved toward a position adjacent the glass, and thereafter the LED can readily be observed while the contact elements engage the glass so that the other hand of the worker is free to support the glass panel or to perform other tasks. In preferred forms of the invention, the contact elements are comprised of a relatively soft metallic material and have a hemispherical configuration for minimizing abrasive damage that could otherwise occur to the coating.

6 Claims, 1 Drawing Sheet

COATING DETECTOR FOR LOW EMISSIVITY GLASS

BACKGROUND OF THE INVENTION

1. Field of the Invention

This invention relates to a detector for measuring the electrical conductivity of planar panels such as sheets of glass having a coated surface on one side thereon, and the detector is particularly adapted for convenient, single handed use in order to free the other hand of the worker for other tasks.

2. Description of the Prior Art

Glazing having a low emissivity coating has been used in an ever-growing share of energy efficient residential and commercial construction in the past few years. Low emissivity glass, or "low-E" glass, includes a thin layer of a coating, typically metal oxide, that is applied to one side of the glass and functions as a selective filter that allows light and near-infrared radiation to pass through the glazing and into the building, while also reflecting long-wave heat that is radiated from materials within the building back toward the interior of the latter. Low emissivity coatings on glass are known to substantially increase the thermal resistance, or R-value, of the glazing, and thereby correspondingly reduce the energy costs for heating and/or cooling of the building. Low emissivity coated glass also offers other advantages over clear, uncoated glass, such as greater comfort to the occupants of the building and reduced fading of fabrics.

Glazing manufacturers increase the thermal resistance of their products by adding additional panes to form dead air spaces which reduce thermal conduction losses. However, a double-glazed window can transfer up to approximately twice as much heat by thermal radiation as compared to the amount of heat transferred by conduction, and thus it is particularly desirable to use a low emissivity coating on one surface of window units which are formed of two spaced, glass panes. In double-glazed units, the low emissivity coating is known to be beneficially effective only when applied to an inner surface of one of the panes in facing relationship to the dead air space.

Currently, two processes are in popular use for coating glass or films. Relatively soft low emissivity coatings are applied by a vacuum deposition process wherein a metal bar is bombarded with electrons and atoms emitted from the bar condense in a vacuum on a cold surface of the glass. Relatively hard low emissivity coatings are made by a pyrolitic process by spraying a hot, thin, metallic oxide coating onto hot glass such that the coating bakes onto the glass surface and hardens as the glass cools. Low emissivity coatings can be comprised of a number of different materials, such as tin oxides or other metallic oxides, or, in some instances, silver or copper.

As mentioned previously, it is of utmost importance that the side of the glass panel which has the low emissivity coating be positioned to face the interior of the dead air insulative space in insulated units which include two or more panes of glass in order for the coating to effectively increase the thermal resistance of the unit. If the glass surface having the coating is mistakenly positioned on an outside surface of one pane of a unit, the problem can go undetected for years and energy costs for the conditioned space will be high. Moreover, the glass of double-glazed units cannot be easily reversed, since such units are permanently sealed at the factory and include a desiccant in the air space to reduce condensation between the panes.

However, during factory assembly of double-paned units, it is generally impossible to visually determine which side, if any, of a glass panel carries a low emissivity coating. In the past, factory workers have typically used a conventional volt-ohmmeter having two flexible, wire-like probes which are both moved by the worker to contact a single side of the glass sheet, since the side having the low emissivity coating exhibits a substantially higher electrical conductivity than the side without the coating. As can be appreciated, use of the ohmmeter with the wire-like probes is somewhat difficult, since it is necessary to use both hands for maneuvering the meter and probes, and consequently the sheet of glass cannot be easily supported by the user at the same time.

SUMMARY OF THE INVENTION

The present invention overcomes the disadvantages of the prior art conductivity sensors by provision of a small, hand-held device including a housing and a pair of spaced apart contact elements that extend outwardly from the housing in fixed orientation relative to the latter. The contact elements are electrically connected to a battery within the housing and a light emitting diode on a wall of the housing, and engagement of the contact elements with a conductive metallic coating completes an electrical circuit and activates the light emitting diode, thus readily indicating to the worker that the contact elements are in engagement with an electrically conductive surface such as a metallic oxide, low emissivity coating on a glass panel. The contact elements are fixedly positioned so that the user can directly and simultaneously engage the planar surface when the housing is brought into adjacent relationship to the panel.

In preferred embodiments of the invention, both of the contact elements include rounded segments for minimizing damage due to abrasion that might otherwise occur when either of the contact elements engages the coating. The rounded shape of the contact elements is particularly desirable when the detector is used for sensing the presence of relatively soft low emissivity coatings which are delicate by nature. Advantageously, the contact elements are made of a soft metallic material such as brass or the like.

The coating detector as disclosed herein takes the form of a small, portable unit which can be easily held by one hand of the worker, thus freeing the remaining hand for supporting the panel to be tested or for other tasks as desired. Once the unit is brought into a position adjacent the pane and both of the contact elements engage the pane surface, observation of the light emitting diode provides an immediate indication as to whether or not the contact elements are in engagement with a conductive, low emissivity coating or, alternatively, in engagement with a relatively non-conductive surface on a side of the pane opposite the coating.

DETAILED DESCRIPTION OF THE DRAWINGS

Figure 1:
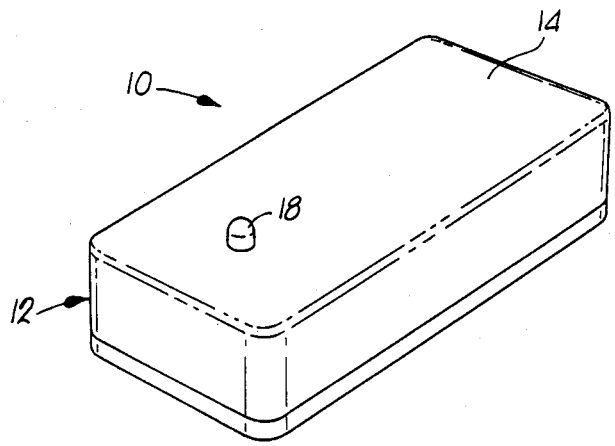
FIG. 1 is a perspective view of the coating detector of the present invention.

A coating detector, as represented in FIGS. 1-5, is designated broadly by the numeral 10 and includes a rectangular in cross-section housing 12 that has a flat, first outer or top wall 14 and a flat, second or bottom outer wall 16 opposite wall 14. The housing 12, including walls 14, 16, are of a small overall configuration adapted to be carried within a palm of the human hand.

Figure 2:
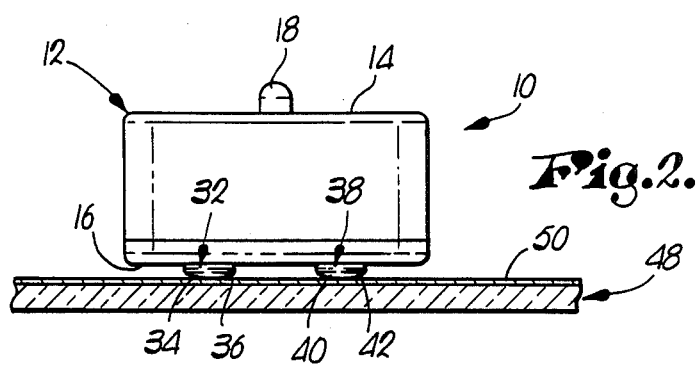
FIG. 2 is a fragmentary, end elevational view of the coating detector of FIG. 1 and a glass panel in section showing two contact elements of the detector in engagement with an electrically conductive, low emissivity coating on one surface of the glass, and also illustrating the position of an indicator means or light emitting diode located on a wall of the detector housing opposite a wall supporting the contact elements.
Figure 4:
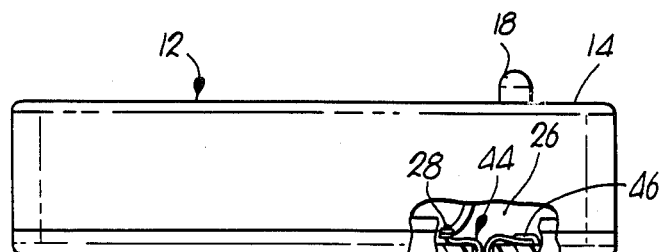
FIG. 4 is a side elevational view of the detector of FIG. 1 with parts broken away in clarity to reveal structure for supporting one of the contact elements a fixed distance away from the outer wall of the housing.
Figure 3:
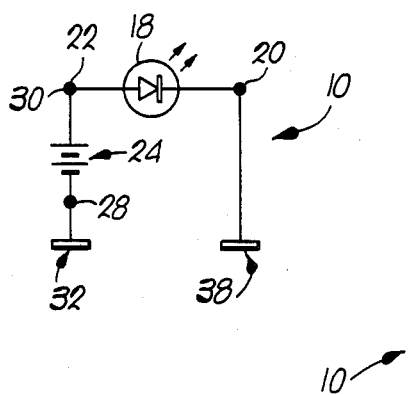
FIG. 3 is an electrical schematic of the circuitry for the detector shown in FIGS. 1 and 2.
Figure 5:
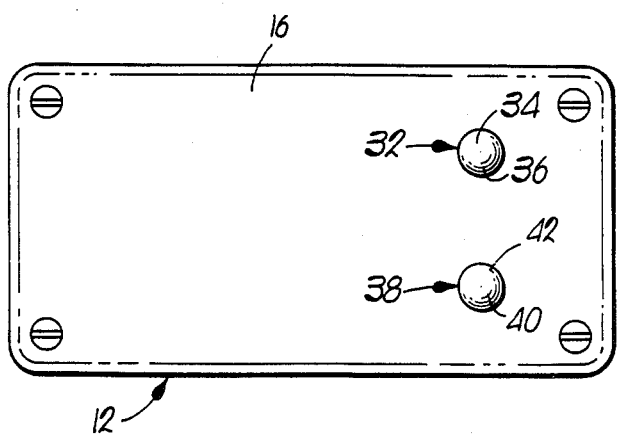
FIG. 5 is a bottom view of the detector shown in FIG. 1.

A on off indicator means, comprising a light emitting diode (LED) 18, is supported by the first wall 14 of the housing 12 as illustrated in FIGS. 1, 2 and 4 and includes a first energizing terminal 20 and a second energizing terminal 22 (see FIG. 3). One or more conventional batteries 24 are carried within a chamber 26 (FIG. 4) of the housing 12 and has a first power terminal 28 (FIG. 3) and a second power terminal 30 which is electrically connected to the second energizing terminal 22 of LED 18.

Viewing FIGS. 2–4, a first contact element 32 has an electrically conductive outer portion 34 that is electrically coupled to the first power terminal 28 of battery 24. The outer portion 34 of the contact element 32 includes rounded segments 36 to present a somewhat hemispherical configuration. A second contact element 38 has an electrically conductive outer portion 40 that is electrically connected to the first energizing terminal 20 of the LED 18, and the outer portion 40 has rounded segments 42 presenting a hemispherical shape similar to the segments 36 of first contact element 32.

Referring to FIG. 4, structure 44 is provided for rigidly connecting the first contact element 32 to the outer, second wall 16 of housing 12 and for supporting the outer portion 34 of the first contact element 32 a fixed distance away from the housing 12. The structure 44 preferably takes the form of a pair of deformable legs that are joined to the first contact element 32. During assembly of the detector unit 10, the structure 44 is inserted through a hole in the second wall 16 of housing 12, and thereafter deformed to tightly engage the second wall 16 of housing 12. Advantageously, a small quantity of adhesive 46 secures structure 44 to the housing 12. Although not illustrated, structure similar to the structure 44 secures the second contact element 38 to the housing 12 for supporting the outer portion 40 of the contact element 38 a fixed distance away from the housing 12.

In use of the detector 10, the housing 12 is grasped by the hand of the worker and shifted toward a position adjacent a planar surface of a body such as a glass panel 48 or the like, as illustrated in FIG. 2. Movement of the detector 10 toward the panel 48 brings the outer portion 34, 40 of contact elements 32, 38 respectively into engagement with an electrically conductive coating 50, comprising, for example, a metal oxide, low emissivity material, that has previously been applied to one side of the glass panel 48. Once both of the contact elements 32, 38 are in electrical engagement with the coating 50, the LED 18 in combination with the battery 24 is operable to emit light for notifying the user that the electrical conductivity of the surface in engagement with the contact elements 32, 38 exceeds a certain, predefined value.

The outer portions 34, 40 are preferably comprised of a relatively soft brass material which, in cooperation with the rounded segments 36, 42 respectively substantially reduces the likelihood of damage that might otherwise occur when the elements 32, 38 are brought into contact with coating 50 of the glass panel 48. Moreover, it is to be noted that the light emitting diode 18 is supported by wall 16 on the opposite side of the housing 12 relative to the wall 14 which supports the contact elements 32, 38, so that light from the LED 18 can be readily observed as soon as both of the contact elements 32, 38 simultaneously touch coating 50.

Those in the art will appreciate that a number of constructional details of the preferred embodiment described above for purposes of illustrating the invention could be modified without departing from the gist and essence of the invention. As such, it is to be understood that the invention is intended to be construed as limited only by the fair scope of the claims that follow and mechanical equivalents thereof.

I claim:

1. A detector for sensing the electrical conductivity of a planar surface of a body such as glass panels and the like comprising:

a housing having outer walls with a configuration adapted to be carried by the human hand;

a battery carried by said housing and having a first power terminal and a second power terminal;

on-off indicator means supported by said housing and having a first energizing terminal and a second energizing terminal electrically connected to said second power terminal of said battery;

a first contact element having an electrically conductive outer portion electrically coupled to said first power terminal of said battery;

a second contact element having an electrically conductive outer portion electrically connected to said first energizing terminal of said indicator means;

said indicator means in combination with said battery being operable to emit a discrete user-notifying signal when said first contact element and said second contact element are in engagement with said surface of said body when the electrical conductivity of said surface exceeds a certain, predefined value; and structure connecting said first contact element and said second contact element to one of said outer walls of said housing for supporting said outer portion of said first contact element and said outer portion of said second contact element a fixed distance away from said housing, for enabling said outer portions to directly and simultaneously engage said planar surface of said body when said housing is brought into a position adjacent said body;

said outer portion of said first contact element and said outer portion of said second contact element including rounded, generally hemispherical segments for minimizing damage due to abrasion on said planar surface of said body.

2. The invention of claim 1, wherein said outer portion of said first contact element and said outer portion of said second contact element comprise a relatively soft metallic material.

3. The invention of claim 2, wherein said outer portion of said first contact element and said outer portion of said second contact element are comprised of a brass material.

4. The invention of claim 1, wherein said indicator means comprises a light emitting diode.

5. The invention of claim 4, wherein one of said outer walls of said housing supports said light emitting diode and is located on an opposite side of said housing relative to the outer wall supporting said contact elements.

6. The invention as set forth in claim 1, wherein said outer walls of said housing include a top wall portion, a bottom wall portion, and opposed side wall portions interconnecting said top wall portion and said bottom wall portion, and wherein said first contact element and said second contact element are carried by said bottom wall portion, and wherein said indicator means is carried by said top wall portion, said top wall portion being substantially devoid of protruding structure and being of a dimension for enabling the hand to extend across said top wall portion in contact with both of said side wall portions while leaving said indicator means exposed, said top wall portion, said bottom wall portion and said side wall portions presenting an overall shape of dimensions to substantially fit within the confines of a clenched hand.

* * * * *